United States Patent
Alsina-Fernandez et al.

(10) Patent No.: US 8,415,296 B2
(45) Date of Patent: Apr. 9, 2013

(54) OXYNTOMODULIN PEPTIDE ANALOGUE

(75) Inventors: Jorge Alsina-Fernandez, Indianapolis, IN (US); Wayne David Kohn, Avon, IN (US)

(73) Assignee: Eli Lilly and Company, Indianapolis, IN (US)

( * ) Notice: Subject to any disclaimer, the term of this patent is extended or adjusted under 35 U.S.C. 154(b) by 247 days.

(21) Appl. No.: 12/968,388

(22) Filed: Dec. 15, 2010

(65) Prior Publication Data

US 2011/0152181 A1 Jun. 23, 2011

Related U.S. Application Data

(60) Provisional application No. 61/352,569, filed on Jun. 8, 2010, provisional application No. 61/288,884, filed on Dec. 22, 2009.

(51) Int. Cl.
*A61K 38/22* (2006.01)
*A61K 38/26* (2006.01)
*A61K 38/28* (2006.01)
*C07K 14/575* (2006.01)
*C07K 7/00* (2006.01)
*C07K 16/00* (2006.01)
*C07K 17/00* (2006.01)

(52) U.S. Cl. ............ 514/4.9; 514/6.9; 514/9.7; 530/324

(58) Field of Classification Search .................. None
See application file for complete search history.

(56) References Cited

U.S. PATENT DOCUMENTS

| | | |
|---|---|---|
| 7,666,835 B2 | 2/2010 | Bloom et al. |
| 7,928,058 B2 * | 4/2011 | Sinha Roy et al. ............. 514/1.1 |
| 8,268,779 B2 * | 9/2012 | Sinha Roy et al. ............. 514/4.8 |
| 2009/0215981 A1 | 8/2009 | Glaesner et al. |
| 2010/0190701 A1 | 7/2010 | Day et al. |

FOREIGN PATENT DOCUMENTS

| | | |
|---|---|---|
| WO | 03022304 A1 | 3/2003 |
| WO | 2004062685 A2 | 7/2004 |
| WO | 2006124529 A1 | 11/2006 |
| WO | 2006134340 A2 | 12/2006 |
| WO | 2007056362 A2 | 5/2007 |
| WO | 2007100535 A2 | 9/2007 |
| WO | 2008071972 A1 | 6/2008 |
| WO | 2008101017 A2 | 8/2008 |
| WO | 2008152403 A1 | 12/2008 |
| WO | 2010096052 A1 | 8/2010 |
| WO | 2010096142 A1 | 8/2010 |

OTHER PUBLICATIONS

Krstenansky et al., Conformational considerations in the design of a glucagon analogue with increased receptor binding and adenylate cyclase potencies, J. Am. Chem. Soc. 1986, pp. 1696-1698, 108.
Gelfanov, et al., Discover and Structural Optimization of High Affinity Co-Agonists at the Glucagon and GLP-1 Receptors, Understanding Biology Using Peptides, Jun. 23, 2005, pp. 763-764, Springer.
Wynne, et al., Subcutaneous Oxyntomodulin Reduces Body Weight in Overweight and Obese Subjects, Diabetes, Aug. 2005, pp. 2390-2395, vol. 54.
Pan, et al., Design of a Long Acting Peptide Functioning as Both a Glucagon-like Peptide-1 Receptor Agonist and a Glucagon Receptor Antagonist, J Biol Chem, May 2006, pp. 12506-12515, 281(18).
Druce, et al., Oxyntomodulin: a novel potential treatment for obesity, Treat Endocrinol, 2006, pp. 265-272, 5(5).
Tom, et al., Reproducible Production of a PEGylated Dual-Acting Peptide for Diabetes, The AAPS Journal, Jun. 2007, pp. E227-E234, 9(2) Article 25.
Maida, et al., The glucagon-like peptide-1 receptor agonist oxyntomodulin enhances beta-cell function but does not inhibit gastric emptying in mice, Endocrinology (2008), pp. 5670-5678, 149(11).
Druce, et al., Investigation of Structure-Activity Relationships of Oxyntomodulin (Oxm) Using Oxm Analogs, Endocrinology, Apr. 2009, pp. 1712-1721, 150(4).
Day, et al., A new glucagon and GLP-1 co-agonist eliminates obesity in rodents, Nature Chemical Biology, Oct. 2009, pp. 749-757, 5(10).

* cited by examiner

*Primary Examiner* — Julie Ha
(74) *Attorney, Agent, or Firm* — Andrea M. Castetter

(57) ABSTRACT

The present invention provides Oxyntomodulin peptide analogues useful in the treatment of diabetes and/or obesity.

18 Claims, No Drawings

OXYNTOMODULIN PEPTIDE ANALOGUE

The present invention relates to Oxyntomodulin peptide analogues and to PEGylated derivatives thereof for use in treating diabetes and/or obesity.

Oxyntomodulin (OXM) is a 37 amino acid peptide hormone that is released along with Glucagon-Like-Peptide 1 (GLP-1) from the L-cells of the small intestine in proportion to nutrient ingestion. It is composed of the full 29 residue sequence of glucagon (Gcg) with an octapeptide extension at the C-terminus as a result of tissue-specific alternate processing of preproglucagon. Endogenous OXM is quickly degraded in vivo by dipeptidyl peptidase IV and other peptidases.

Distinct receptors for OXM have not yet been identified. OXM binds to and fully activates both the GLP-1 receptor (GLP-1R) and the glucagon receptor (GcgR) in vitro with similar potencies at the two receptors.

OXM is involved in regulation of food intake and body weight. Acute administration of OXM to normal-weight human subjects reduced hunger and decreased meal size by 19%. In a 4-week study with overweight and obese subjects, three times daily preprandial subcutaneous administration of OXM produced a weight loss of 2.3 kg compared with 0.5 kg in the placebo group. In this trial, nausea, the most common side effect associated with GLP-1 based therapy (such as exenatide and liraglutide), was significantly less prevalent. OXM increased energy usage through promotion of increased physical activity in overweight and obese humans, although the mechanism of the effect is unclear.

OXM presents several challenges for development into a commercially-viable therapeutic agent. As mentioned above, it is rapidly degraded in vivo as well as being subjected to rapid renal clearance due to its small size. It is therefore desirable to identify OXM peptide analogues with improved metabolic stability and reduced rate of clearance. Furthermore, the GcgR agonist activity inherent in OXM presents a risk of negatively impacting glycemic control. Thus, it is also desirable to optimize the potency of an OXM peptide analogue designed for therapeutic use while maintaining an appropriate balance between activities at the GLP-1R and GcgR. Activation of GLP-1R is responsible for an insulinotropic effect while activation of both GLP-1R and GcgR may play a role in the weight loss effects. It is therefore desirable to produce an OXM peptide analogue which has potent insulinotropic activity and promotes weight loss such that it can be used for the treatment of non-insulin dependent diabetes and/or obesity.

OXM peptides with amino acid substitutions to improve stability and with additional modifications to slow clearance, such as PEGylation or lipidation are disclosed in WO 2008101017, WO2006134340, WO2007100535, and Pocai et al. *Diabetes* 58:2258-2266, 2009. While these OXM-derived peptides may represent a potential improvement over the wild type peptide, the doses required to achieve a sizable weight reduction in a diet-induced obese (DIO) mouse model are typically higher than may be considered feasible for pharmaceutical commercialization. For example, Pocai et al (2009) reported an average 11 g (~25%) weight loss after 13 days of dosing with 1900 nmol/kg (~8 mg/kg) every other day (QOD).

Despite the availability of various OXM peptides and analogues thereof, there is still a need for more potent, stable, long-acting, and well-tolerated OXM peptide analogues having a ratio of GcgR/GLP-1R activity which has been optimized such that the potency and insulinotropic activity of the peptide provides effective treatments for diabetes, preferably type 2 diabetes and related disorders. It is also desirable to provide OXM peptide analogues thereof which provide effective treatments to reduce body weight. Accordingly, the present invention seeks to provide effective treatments for diabetes and/or obesity.

The present invention comprises an OXM peptide analogue with amino acid substitutions introduced to optimize metabolic stability and modulate the relative GcgR/GLP-1R activities while optimizing overall potency. In addition, the OXM peptide analogue of the present invention is PEGylated at selected positions for enhancement of time action thereby allowing for less frequent dosing.

The present invention provides an Oxyntomodulin peptide analogue comprising the amino acid sequence:

```
                                          (SEQ ID NO: 5)
1                   5                      10
His-(D-Ser)-Gln-Gly-Thr-Phe-Thr-Ser-Asp-(1-Nal)-

15                     20
Ser-Lys-Tyr-Leu-Asp-Glu-Lys-Ala-Ala-Gln-Glu-Phe- 25                  30
Val-Gln-Trp-Leu-Leu-Asn-(Aib)-Ala-Arg-Asn-Arg-

35
Asn-Asn-Ile-Ala-Xaa38-Xaa39
``` wherein $Xaa_{38}$ is Cys, Cys-PEG, or is absent, $Xaa_{39}$ is Cys, Cys-PEG, or is absent, and wherein the C-terminal amino acid is optionally amidated.

The present invention provides an Oxyntomodulin peptide analogue comprising the amino acid sequence:

```
                                          (SEQ ID NO: 1)
1                   5                      10
His-(D-Ser)-Gln-Gly-Thr-Phe-Thr-Ser-Asp-(1-Nal)-

15                     20
Ser-Lys-Tyr-Leu-Asp-Glu-Lys-Ala-Ala-Gln-Glu-Phe- 25                  30
Val-Gln-Trp-Leu-Leu-Asn-(Aib)-Ala-Arg-Asn-Arg-

35
Asn-Asn-Ile-Ala.
```

Furthermore, the present invention provides an Oxyntomodulin peptide analogue comprising the amino acid sequence:

```
                                          (SEQ ID NO: 2)
1                   5                      10
His-(D-Ser)-Gln-Gly-Thr-Phe-Thr-Ser-Asp-(1-Nal)-

15                     20
Ser-Lys-Tyr-Leu-Asp-Glu-Lys-Ala-Ala-Gln-Glu-Phe- 25                  30
Val-Gln-Trp-Leu-Leu-Asn-(Aib)-Ala-Arg-Asn-Arg-

35
Asn-Asn-Ile-Ala-Cys-Cys
``` wherein the Cys at position 38 is optionally PEGylated, and wherein the Cys present at position 39 is optionally PEGylated and the carboxyl group of the Cys at position 39 is optionally amidated.

Preferably, the Oxyntomodulin peptide analogue of SEQ ID NO: 2 is PEGylated on either the Cys at position 38 or the Cys at position 39 or both with a 40 kDa PEG molecule covalently linked to the thiol group of the Cys residue at these positions. More preferably the Oxyntomodulin peptide analogue is PEGylated on each Cys residue at both position 38 and position 39 with a 20 kDa PEG molecule covalently linked to each thiol group of each Cys residue at these positions. Optionally, the Cys residue at position 39 may be absent from SEQ ID NO: 2, leaving a single site for PEGylation at position 38.

The more preferred Oxyntomodulin peptide analogue comprises the amino acid sequence:

```
                                              (SEQ ID NO: 3)
1               5                        10
His-(D-Ser)-Gln-Gly-Thr-Phe-Thr-Ser-Asp-(1-Nal)-

15                        20
Ser-Lys-Tyr-Leu-Asp-Glu-Lys-Ala-Ala-Gln-Glu-Phe- 25                    30
Val-Gln-Trp-Leu-Leu-Asn-(Aib)-Ala-Arg-Asn-Arg-

35
Asn-Asn-Ile-Ala-Cys(20 kDa PEG)-

Cys(20 kDa PEG)
``` wherein the carboxyl group of the PEGylated Cys at position 39 is optionally amidated.

The most preferred Oxyntomodulin peptide analogue comprises the amino acid sequence of SEQ ID NO: 3, wherein the carboxyl group of the PEGylated Cys at position 39 is amidated.

The PEG molecule used in the present invention may be linear or branched and is preferably a linear PEG molecule.

The present invention provides a pharmaceutical composition comprising the Oxyntomodulin peptide analogue as defined above, and a pharmaceutically acceptable carrier, diluent, or excipient. Additionally, the present invention provides a pharmaceutical composition comprising the Oxyntomodulin peptide analogue as defined above, together with a pharmaceutically acceptable carrier, diluent, or excipient and optionally other therapeutic ingredients.

Furthermore, the present invention provides a method of treating non-insulin-dependent (type 2) diabetes in a subject in need thereof, comprising administering to the subject in need thereof an effective amount of an Oxyntomodulin peptide analogue as defined above.

Additionally, the present invention provides a method of treating insulin-dependent (type 1) diabetes in a subject in need thereof, comprising administering to the subject in need thereof an effective amount of an Oxyntomodulin peptide analogue as defined above.

The present invention includes a method of treating obesity in a subject in need thereof, comprising administering to the subject in need thereof an effective amount of an Oxyntomodulin peptide analogue as defined above.

Furthermore, the present invention includes a method of treating non-insulin-dependent diabetes and obesity in a subject in need thereof, comprising administering to the subject in need thereof an effective amount of an Oxyntomodulin peptide analogue as defined above.

The present invention provides an Oxyntomodulin peptide analogue as defined above for use as a medicament.

Additionally, the present invention provides an Oxyntomodulin peptide analogue as defined above for use in the treatment of non-insulin-dependent diabetes.

Furthermore, the present invention provides an Oxyntomodulin peptide analogue as defined above for use in the treatment of insulin-dependent diabetes.

Furthermore, the present invention provides an Oxyntomodulin peptide analogue as defined above for use in the treatment of obesity.

The present invention includes an Oxyntomodulin peptide analogue as defined above for use in the treatment of non-insulin-dependent diabetes and obesity.

The present invention provides the use of an Oxyntomodulin peptide analogue as defined above in the manufacture of a medicament for the treatment of non-insulin-dependent diabetes.

Additionally, the present invention includes the use of an Oxyntomodulin peptide analogue as defined above in the manufacture of a medicament for the treatment of insulin-dependent diabetes.

Furthermore, the present invention provides the use of an Oxyntomodulin peptide analogue as defined above in the manufacture of a medicament for the treatment of obesity.

Furthermore, the present invention provides the use of an Oxyntomodulin peptide analogue as defined above in the manufacture of a medicament for the treatment of non-insulin-dependent diabetes and obesity.

The OXM peptide analogues of the present invention effectively bind to and activate both the GLP-1 receptor (GLP-1R) and glucagon receptor (GcgR).

It has also been found that the OXM peptide analogues of the present invention are more resistant to degradation by peptidases, in particular dipeptidyl peptidase IV than native human OXM. As a result, the OXM peptide analogues of the present invention possess improved in vivo stability versus native human OXM.

Various embodiments according to the present invention are capable of causing a reduction in food intake in overweight and obese subjects.

A particular advantage of the present invention is that the frequency of side-effects, such as nausea, which is commonly associated with GLP-1 based therapy, such as exenatide and liraglutide, is reduced or eliminated. The present invention therefore has reduced side-effects compared to GLP-1 based therapy.

The OXM peptide analogues of the present invention also have superior weight loss effect versus wild type human OXM.

Oxyntomodulin (OXM) is a weak co-agonist with full efficacy and balanced potency at the hGLP-1R and hGcgR, with $EC_{50}$ values of about 6.7±2.7 nM and 4.1±1.7 nM, respectively in HEK293 cells stably overexpressing the respective receptors. The sequence of native human OXM is given below:

```
                                              (SEQ ID NO: 4)
His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Met-Asn-Thr-Lys-Arg-Asn-Arg-Asn-Asn-Ile-

Ala
```

The OXM peptide analogue of SEQ ID NO: 3 wherein the Cys(PEG20k) at position 39 is amidated is a fully efficacious and potent Oxyntomodulin peptide analogue with an $EC_{50}$ of 60.0±2.97 nM and 6.58±0.87 nM against the hGcgR and hGLP-1R, respectively. The OXM peptide analogue of SEQ ID NO: 3 wherein the Cys(PEG20k) at position 39 is amidated has a balance of in vitro functional activities that is ~9-fold more selective for the hGLP-1R as compared to hGcgR. Comparable results are observed for the binding affinities, Ki, where the OXM peptide analogue of SEQ ID NO: 3 wherein the Cys(PEG20k) at position 39 is amidated is 3.6-fold more selective for the hGLP-1R as compared to the hGcgR, with Ki values of 1540±158 nM and 5500±350 nM, respectively.

The covalent attachment of one or more molecules of PEG to particular residues of the OXM peptide analogue results in a PEGylated OXM peptide analogue with an extended half-life and reduced rate of clearance, when compared to that of the non-PEGylated OXM peptide analogue, and in vitro potency at the GLP-1R similar to that of native human OXM. Given the small size of the OXM peptide analogue and the relatively large size of the PEG molecule(s), it would be expected that the OXM peptide analogue, once PEGylated, would lose activity as a result of steric hindrance. It has been found, however, that if placed at the end of the Oxyntomodulin peptide analogue rather than in the middle, the activity of the peptide analogue is retained to a greater extent. Several substitutions in the sequence enhance potency, thereby offsetting the potency loss due to PEGylation while maintaining an appropriate ratio of activities at the GLP-1R and GcgR. Furthermore, it has been found that the presence of two PEG molecules at the C-terminal end of the OXM peptide analogue is preferable to a single PEG.

The sequences of the present invention contain the standard single letter or three letter codes for the twenty naturally-occurring amino acids. The other codes used are defined as follows:
  d or D=the D isoform (nonnaturally occurring) of the respective amino acid, e.g., D-Ser=D-Serine, dS=D-Serine
  Aib=alpha amino isobutyric acid
  1-Nal=1-naphthylalanine
  PEG=polyethylene glycol
  PEG20K=PEG molecule with average molecular weight of 20,000 Da The term "PEG" as used herein means a polyethylene glycol molecule. In its typical form, PEG is a linear polymer with terminal hydroxyl groups and has the formula HO—CH$_2$CH$_2$—(CH$_2$CH$_2$O)n-CH$_2$CH$_2$—OH, where n is from about 8 to about 4000. Typically, n is not a discrete value but constitutes a range with approximately Gaussian distribution around an average value. The terminal hydrogen may be substituted with a capping group such as an alkyl or alkanol group. Preferably, PEG has at least one hydroxy group, more preferably it is a terminal hydroxy group. This hydroxy group is preferably attached to a linker moiety, which can react with the peptide to form a covalent linkage. Numerous derivatives of PEG exist in the art. (See, e.g., U.S. Pat. Nos. 5,445,090; 5,900,461; 5,932,462; 6,436,386; 6,448,369; 6,437,025; 6,448,369; 6,495,659; 6,515,100 and 6,514,491 and Zalipsky, S. *Bioconjugate Chem.* 6:150-165, 1995). The PEG molecule covalently attached to the OXM peptide of the present invention may be approximately 10,000, 20,000, 30,000, or 40,000 daltons average molecular weight. The PEG molecule is preferably 18,000 to 22,000 daltons. More preferably, it is 19,000 to 21,000 Daltons. Most preferably it is 20,000 to 21,000 daltons. It is even more preferably approximately 20,000 daltons. PEGylation reagents may be linear or branched molecules and may be present singularly or in tandem. The PEGylated OXM peptide analogues of the present invention preferably have tandem PEG molecules attached to the C-terminus of the peptide. The PEG molecules are preferably attached to the two cysteine residues at the C-terminal end of the peptide by an mPEG-20 kDa maleimide (Formula 1) or an mPEG-20 kDa iodoacetamide (Formula 2). In Formula 1 and Formula 2, n is 10 to 2500. Preferably, n is 350 to 600. More preferably, n is 425 to 475.

Formula 1

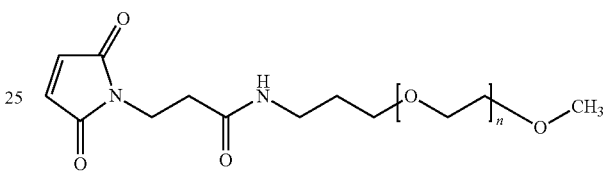

Formula 2

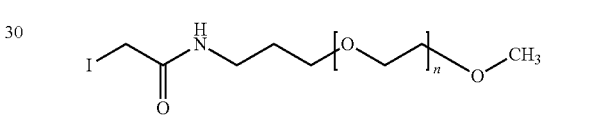

In particular, the PEG molecules are preferably mPEG-20 kDa maleimide (CH$_3$O(CH$_2$CH$_2$O)$_n$—(CH$_2$)$_3$NHCO(CH$_2$)$_2$-maleimide) (NOF Sunbright ME-200MA) and are attached to the two cysteine residues at the C terminus of the peptide. The most preferred Oxyntomodulin peptide analogue comprises the amino acid sequence of SEQ ID NO: 3, wherein the PEG molecules are mPEG-20 kDa maleimide (CH$_3$O(CH$_2$CH$_2$O)$_n$—(CH$_2$)$_3$NHCO(CH$_2$)$_2$-maleimide) (NOF Sunbright ME-200MA), and wherein the carboxyl group of the PEGylated Cys at position 39 is amidated (Formula 3). Formula 3 contains the standard single letter amino acid code with exception of the box areas where the structures for these amino acid residues have been expanded.

Formula 3

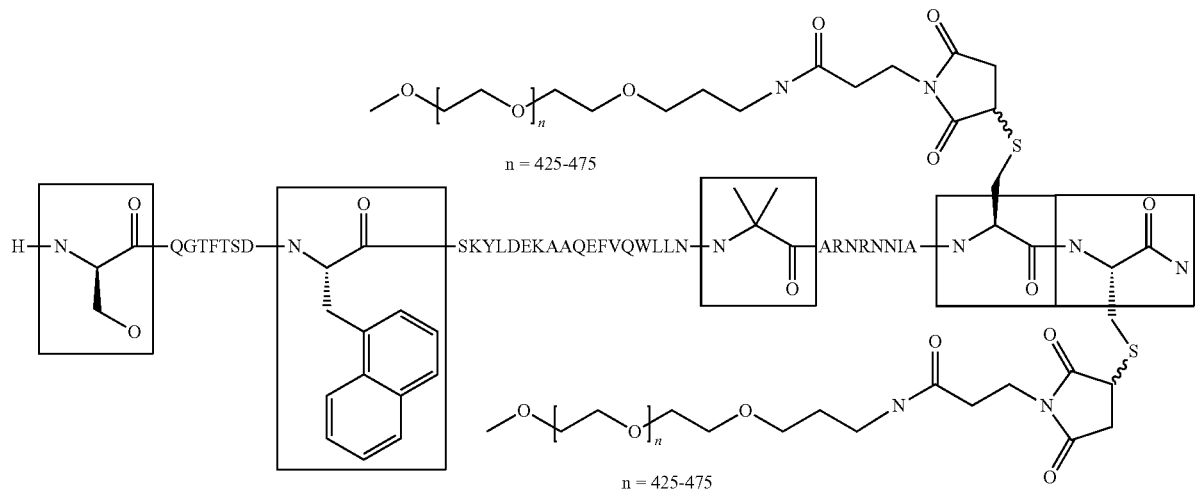

The term "PEGylation" as used herein means the covalent attachment of one or more PEG molecules, as described above, to a molecule such as the OXM peptide analogues of the present invention.

"Insulinotropic activity" refers to the ability to stimulate insulin secretion in response to elevated glucose levels, thereby causing glucose uptake by cells and decreased plasma glucose levels. Insulinotropic activity can be assessed by methods known in the art, including in vitro experiments that measure insulin secretion by insulinoma cell lines or islets or in vivo experiments such as intravenous glucose tolerance test (IVGTT), intraperitoneal glucose tolerance test (IPGTT), and oral glucose tolerance test (OGTT). Insulinotropic activity is routinely measured in humans by measuring plasma insulin or C-peptide levels. The OXM peptide analogues of the present invention possess robust insulinotropic activity.

"In vitro potency" as used herein is the measure of the ability of the OXM peptide analogue to activate the GLP-1R or the GcgR in a cell-based assay. In vitro potency is expressed as the "$EC_{50}$," which is the effective concentration of compound that results in a half maximal increase in the measured response (in this case, cyclic AMP production) in a dose-response experiment.

The term "plasma half-life" refers to the time required for half of the relevant molecules to be cleared from the plasma. An alternatively used term is "elimination half-life." The term "extended" or "longer" used in the context of plasma half-life or elimination half-life indicates there is a significant increase in the half-life of a PEGylated OXM peptide analogue relative to that of the reference molecule (e.g., the non-PEGylated form of the peptide or the native peptide) as determined under comparable conditions. The half-life of native OXM in monkeys, for example, is expected to be less than 1 hr. The PEGylated OXM peptide analogues of the present invention have an elimination half-life of at least 24 hr in monkey, and preferably at least 48 hours. The half-life reported herein is the elimination half-life, which corresponds to the terminal log-linear rate of elimination. The person skilled in the art appreciates that half-life is a derived parameter that changes as a function of both clearance and volume of distribution.

The term "long-acting GLP-1R agonist" as used herein, refers to a GLP-1 peptide analogue covalently attached to one or more molecules of polyethylene glycol (PEG). PEGylated GLP-1 compounds are disclosed in U.S. Pat. No. 7,557,183.

Clearance is the measure of the body's ability to eliminate a drug from circulation. As clearance decreases due, for example, to modifications to a drug, half-life would be expected to increase. However, this reciprocal relationship is exact only when there is no change in the volume of distribution. A useful approximate relationship between the terminal log-linear half-life ($t_{1/2}$), clearance (C), and volume of distribution (V) is given by the equation: $t_{1/2} \approx 0.693$ (V/C). Clearance does not indicate how much drug is being removed but, rather, the volume of biological fluid such as blood or plasma that would have to be completely freed of drug to account for the elimination. Clearance is expressed as a volume per unit of time. The PEGylated OXM peptide analogues of the present invention preferably have a clearance value of 200 ml/h/kg or less in monkeys, more preferably 180, 150, 120, 100, 80, 60 ml/h/kg or less and most preferably 50, 40 or 20 ml/h/kg or less.

The OXM peptide analogues of the present invention typically will be administered parenterally. Parenteral administration includes, for example, systemic administration, such as by intramuscular, intravenous, subcutaneous, intradermal, or intraperitoneal injection. The peptide analogue is administered to the subject in conjunction with an acceptable pharmaceutical carrier, diluent, or excipient as part of a pharmaceutical composition for treating non-insulin dependent (type 2) diabetes mellitus, NIDDM, or the related disorders discussed below. The pharmaceutical composition can be a solution or a suspension of the OXM peptide analogue, such as one in which the OXM peptide analogue is complexed with a divalent metal cation such as zinc. The peptide analogue may also be formulated in a solid formulation such as by lyophilisation or spray-drying, which is then reconstituted in a suitable diluent solution prior to administration. Suitable pharmaceutical carriers may contain inert ingredients which do not interact with the peptide or peptide derivative. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Some examples of suitable excipients include lactose, dextrose, sucrose, trehalose, sorbitol, and mannitol and preservatives such as phenol and m-cresol.

Standard pharmaceutical formulation techniques, such as those described in Remington's Pharmaceutical Sciences (Mack Publishing Company, Easton, Pa.), may be employed. The OXM peptide analogues of the present invention may alternatively be formulated for administration through the buccal, oral, transdermal, nasal, or pulmonary route. The OXM peptide analogues of the invention may be formulated for extended release such that blood plasma levels are maintained in the efficacious range for extended time periods after administration.

The OXM peptide analogues of the present invention may be employed to treat diabetes, specifically type 2 diabetes (non-insulin dependent diabetes mellitus or NIDDM). Additional subjects who may benefit from treatment with the OXM peptide analogues of the present invention include those with impaired glucose tolerance or impaired fasting glucose, subjects whose body weight is about 25% or more above normal body weight for the subject's height and body build, subjects having one or more parents with NIDDM, subjects who have had gestational diabetes, and subjects with metabolic disorders such as those resulting from decreased endogenous insulin secretion. The OXM peptide analogue may be used to prevent subjects with impaired glucose tolerance from proceeding to develop type 2 diabetes, prevent pancreatic β-cell deterioration, induce β-cell proliferation, improve β-cell function, activate dormant β-cells, promote differentiation of cells into β-cells, stimulate β-cell replication, and inhibit β-cell apoptosis. Other diseases and conditions that may be treated or prevented using compounds of the invention in methods of the invention include: Maturity-Onset Diabetes of the Young (MODY) (Herman, et al., *Diabetes* 43:40, 1994); Latent Autoimmune Diabetes Adult (LADA) (Zimmet, et al., *Diabetes Med.* 11:299, 1994); impaired glucose tolerance (IGT) (Expert Committee on Classification of Diabetes Mellitus, *Diabetes Care* 22 (Supp. 1):S5, 1999); impaired fasting glucose (IFG) (Charles, et al., *Diabetes* 40:796, 1991); gestational diabetes (Metzger, *Diabetes,* 40:197, 1991); metabolic syndrome X, dyslipidemia, hyperglycemia, hyperinsulinemia, hypertriglyceridemia, and insulin resistance.

The OXM peptide analogues of the invention may also be used in methods of the invention to treat secondary causes of diabetes (Expert Committee on Classification of Diabetes Mellitus, *Diabetes Care* 22 (Supp. 1):S5, 1999). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenyloin, thyroid hormone, β-adrenergic agents, α-interferon and drugs used to treat HIV infection.

The OXM peptide analogues of the present invention may be effective in the suppression of food intake and the treatment of obesity.

An "effective amount" of an OXM peptide analogue is the quantity that results in a desired therapeutic and/or prophylactic effect without causing unacceptable side effects when administered to a subject. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of an OXM peptide analogue for the treatment of NIDDM is the quantity that would result in greater control of blood glucose concentration than in the absence of treatment, thereby resulting in a delay in the onset of diabetic complications such as retinopathy, neuropathy, or kidney disease. An "effective amount" of an OXM peptide analogue for the prevention of NIDDM, for example in subjects with impaired glucose tolerance or impaired fasting glucose, is the quantity that would delay, compared with the absence of treatment, the onset of elevated blood glucose levels that require treatment with anti-hyperglycemic drugs such as sulfonylureas, thiazolidinediones, insulin, and/or bisguanidines.

An "effective amount" of an OXM peptide analogue administered to a subject will also depend on the type and severity of the disease and on the characteristics of the subject, such as general health, age, sex, body weight and tolerance to drugs. The dose of OXM peptide analogue effective to normalize a subject's blood glucose will depend on a number of factors, among which are included, without limitation, the subject's sex, weight and age, the severity of inability to regulate blood glucose, the route of administration and bioavailability, the pharmacokinetic profile of the peptide, the potency, and the formulation.

A typical once weekly dose for the PEGylated OXM peptide analogues of the present invention preferably will range from about 0.1 mg to about 1000 mg (total weight of the conjugate). More preferably, the once weekly dose will range from about 1 mg to about 100 mg, or about 1 mg to about 30 mg. Most preferably, the once weekly dose will range from about 5 mg to about 30 mg, or about 1 mg to about 5 mg.

A "subject" is a mammal, preferably a human, but can also be an animal, including companion animals (e.g., dogs, cats, and the like), farm animals (e.g., cows, sheep, pigs, horses, and the like) and laboratory animals (e.g., rats, mice, guinea pigs, and the like).

Various preferred features and embodiments of the present invention will now be described only by way of the examples.

EXAMPLE 1

Peptide Synthesis

The peptide analogue according to SEQ ID NO: 1 and SEQ ID NO: 2 of the present invention is generated by solid-phase peptide synthesis on a Protein Technologies Inc. Symphony or Applied Biosystems 433A automated peptide synthesizer. Synthesis is performed on Fmoc-Rink amide polystyrene resin (Rapp Polymere Tubingen, Germany) with substitution approximately 0.7 mmol/g. The synthesis is performed using the Fmoc main-chain protecting group strategy. Amino acid side-chain derivatives used are: Arg(Pbf), Asn(Trt), Asp (OtBu), Cys(Trt), Gln(Trt), Glu(OtBu), His(Trt), Lys(Boc), Ser(OtBu), Thr(OtBu), Trp(Boc) and Tyr(OtBu). Coupling is carried out with approximately 10 equivalents of amino acid activated with diisopropylcarbodiimide (DIC) and hydroxybenzotriazole (HOBt) (1:1:1 molar ratio) in dimethylformamide (DMF) or N-methylpyrrolidinone (NMP). Coupling is carried out for 45 to 90 minutes at room temperature.

Concomitant cleavage from the resin and side chain protecting group removal are carried out in a solution containing trifluoroacetic acid (TFA): triisopropylsilane: 3,6-dioxa-1,8-octane-dithiol: methanol: anisole 90:4:2:2:2 (v/v) for 1.5 to 2 hours at room temperature. The solution is filtered and concentrated to <2 mL, and peptides are precipitated with cold diethyl ether, redissolved in 30-40 mL of 10% acetonitrile and purified on a $C_{18}$ reversed-phase high performance liquid chromatography (HPLC) column (typically a Waters SymmetryPrep 7 um, 19×300 mm) at a flow rate of 12-15 mL/min. Samples are eluted with a two-stage linear AB gradient of 0 to 25% B over 20 minutes followed by 25 to 75% B over 100 minutes where A=0.05% TFA/water and B=0.05% TFA/acetonitrile. Product generally elutes at 30-35% acetonitrile. Peptide purity and molecular weight is confirmed on an Agilent 1100 Series liquid chromatography-mass spectrometry (LC-MS) system with a single quadrupole MS detector. Analytical HPLC separation is done on a Zorbax Eclipse XDB-C8, 5 micron, 4.6 mm i.d.×15 cm column with a linear AB gradient of 6 to 60% B over 15 minutes in which A=0.05% TFA/$H_2O$ and B=0.05% TFA/acetonitrile and the flow rate is 1 ml/min. The peptide analogue is purified to >95% purity and is confirmed to have molecular weight corresponding to the calculated value within 1 atomic mass unit (amu).

EXAMPLE 2

PEGylation of Peptide Containing Two Cys Residues with mPEG-MAL-20 kDa

The lyophilized peptide analogue (SEQ ID NO: 2) generated according to Example 1 is weighed out (typically 30-50 mg). A 2.1 fold molar equivalent of mPEG-20 kDa maleimide ($CH_3O(CH_2CH_2O)_n$—$(CH_2)_3NHCO(CH_2)_2$-maleimide) (NOF Sunbright ME-200MA) is weighed out and combined with the peptide. The reactants are dissolved in a 50/50 (v/v) water/acetonitrile mixture to a peptide concentration of approximately 20 mg/mL. The peptide analogue solution is diluted two-fold with 100 mM ammonium acetate, 10 mM ethylenediaminetetraacetic acid (EDTA), pH 7. The resultant mixture is then stirred at room temperature. The reaction mixture is monitored by analytical reversed phase HPLC (analytical HPLC separation is done on a Waters SymmetryShield C18, 3.5 micron, 4.6 mm i.d.×10 cm column at 50° C. with a two-stage linear AB gradient of 0 to 30% B over 5 minutes and 30 to 90% B over the subsequent 30 min in which A=0.05% TFA/$H_2O$ and B=0.05% TFA/acetonitrile and the flow rate is 1 ml/min), and typically after 1-2 hr reaction time, shows almost complete disappearance of the peptide peak. Two peaks due to mono- and di-PEGylated peptide appear with the di-PEGylated peptide typically constituting 90-95% of the total peak area. The sample is then diluted to about 20 mL with water and purified as in Example 1 with a two-stage linear AB gradient of 0 to 30% B over 20 min followed by 30 to 80% B over 100 min. Product generally elutes at 35-40% acetonitrile. The purified peptide is quantitated by ultraviolet (UV) absorbance at 280 nm using a calculated molar extinction coefficient based on the peptide sequence. Yield after purification is in the range of 70 to 80% based on the amount of starting peptide.

EXAMPLE 3

Glucagon Receptor (hGcgR) Binding Assay

The Glucagon receptor binding assay utilizes cloned human glucagon receptor (hGcgR) (Lok S, Kuijper J L, Jelinek L J, Kramer J M, Whitmore T E, Sprecher C A, Mathewes S, Grant F J, Biggs S H, Rosenberg G B, et al. Gene 140 (2), 203-209 (1994)) isolated from 293HEK membranes. The hGlucR cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA is transfected into 293HEK cells and selected with 200 µg/ml Hygromycin.

Crude plasma membranes are prepared using cells from suspension culture. The cells are lysed on ice in hypotonic buffer containing 25 mM Tris HCl, pH 7.5, 1 mM $MgCl_2$, DNAse1, 20 ug/ml, and Roche Complete Inhibitors without EDTA. The cell suspension is homogenized with a glass dounce homogenizer using a Teflon pestle for 25 strokes. The homogenate is centrifuged at 4° C. at 1800×g for 15 minutes. The supernatant is collected and the pellet is resuspended in hypotonic buffer and rehomogenized. The mixture is centrifuged at 1800×g for 15 minutes. The second supernatant is combined with the first supernate. The combined supernatants are centrifuged at 1800×g for 15 minutes to clarify. The clarified supernatant is transferred to high speed tubes and centrifuged at 25000×g for 30 minutes at 4° C. The membrane pellet is resuspended in homogenization buffer and stored as frozen aliquots at −80° C. freezer until use.

Glucagon is radioiodinated by $^{125}$I-lactoperoxidase procedure and purified by reversed phase HPLC at Perkin-Elmer/NEN (NEX207). The specific activity is about 2200 Ci/mmol $K_D$ determination is performed by homologous competition instead of saturation binding due to high propanol content in the $^{125}$I-labelled glucagon material. The $K_D$ is estimated to be 2.62 nM and is used to calculate Ki values for all compounds tested.

The receptor binding assay is carried out using a Scintillation Proximity Assay (SPA) with wheat germ agglutinin (WGA) beads previously blocked with 1% fatty acid free bovine serum albumin (BSA). The binding buffer contains 25 mM 4-(2-hydroxyethyl)-1-piperazineethanesulfonic acid (HEPES), pH 7.4, 2.5 mM $CaCl_2$, 1 mM $MgCl_2$, 0.1% fatty acid free BSA, 0.003% Tween20, and Roche Complete Inhibitors without EDTA. Glucagon is dissolved in 0.01 N HCl at 1 mg/ml and immediately frozen at −80° C. in 30 µl aliquots. Glucagon aliquots are diluted and used in the binding assay within 1 hr. The OXM peptide analogue is dissolved in phosphate buffered saline (PBS) and serially diluted in binding buffer. Next, 10 µl diluted compounds or PBS is transferred into Corning 3632 clear bottom assay plates containing 40 µl assay binding buffer or cold glucagon (non-specific binding (NSB) at 1 µM final). Then, 90 µl membranes (3 µg/well), 50 µl $^{125}$I-Glucagon (0.15 nM final concentration in reaction), and 50 µl of WGA beads (150 µg/well) are added. Plates are sealed, mixed end over end, and read with a MicroBeta scintillation counter after 12 hr of settling time at room temperature.

Results are calculated as a percent of specific $^{125}$I-glucagon binding in the presence of compound. The absolute $IC_{50}$ concentration of compound is derived by non-linear regression of percent specific binding of $^{125}$I-glucagon vs. the concentration of compound added. The $IC_{50}$ dose is converted to Ki using the Cheng-Prusoff equation (Cheng Y., Prusoff W. H., Biochem. Pharmacol. 22, 3099-3108, 1973). The Ki of the OXM peptide analogue of SEQ ID NO: 3 wherein the Cys (PEG20k) at position 39 is amidated was 5500±350 nM for hGcgR binding.

EXAMPLE 4

Glucagon-Like-Peptide 1 (hGLP-1-R) Receptor Binding Assay

The GLP-1 receptor binding assay uses cloned human glucagon-like peptide 1 receptor (hGLP-1R) (Graziano M P, Hey P J, Borkowski D, Chicchi G G, Strader C D, Biochem Biophys Res Commun. 1993 Oct. 15; 196(1):141-6) isolated from 293HEK membranes. The hGLP-1R cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA is transfected into 293HEK cells and selected with 200 µg/ml Hygromycin.

Crude plasma membranes are prepared using cells from suspension culture. The cells are lysed on ice in hypotonic buffer containing 25 mM Tris HCl, pH 7.5, 1 mM $MgCl_2$, DNAse1, 20 ug/ml, and Roche Complete Inhibitors without EDTA. The cell suspension is homogenized with a glass dounce homogenizer using a Teflon pestle for 25 strokes. The homogenate is centrifuged at 4° C. at 1800×g for 15 minutes. The supernatant is collected and the pellet is resuspended in hypotonic buffer and rehomogenized. The mixture is centrifuged at 1800×g for 15 minutes. The second supernatant is combined with the first supernatant. The combined supernatants are centrifuged at 1800×g for 15 minutes to clarify. The clarified supernatant is transferred to high speed tubes and centrifuged at 25000×g for 30 minutes at 4° C. The membrane pellet is resuspended in homogenization buffer and stored as frozen aliquots at −80° C. freezer until use.

Glucagon-like peptide 1 (GLP-1) is radioiodinated by the $^{125}$I-lactoperoxidase procedure and purified by reversed phase HPLC at Perkin-Elmer/NEN (NEX308). The specific activity is about 2200 Ci/mmol $K_D$ determination is performed by homologous competition instead of saturation binding due to high propanol content in the $^{125}$I-GLP-1 material. The $K_D$ is estimated to be 0.96 nM and is used to calculate Ki values for all compounds tested.

The receptor binding assay is carried out using a Scintillation Proximity Assay (SPA) with wheat germ agglutinin (WGA) beads previously blocked with 1% fatty acid free BSA (ICN). The binding buffer contains 25 mM HEPES, pH 7.4, 2.5 mM $CaCl_2$, 1 mM $MgCl_2$, 0.1% fatty acid free BSA, 0.003% Tween20, and Roche Complete Inhibitors without EDTA. GLP-1 is dissolved in PBS at 1 mg/ml and immediately frozen at −80° C. in 30 µl aliquots. GLP-1 aliquots are diluted and used in binding assays within 1 hr. The OXM peptide analogue is dissolved in PBS and serially diluted in binding buffer. Next, 10 µl diluted compounds or PBS is transferred into Corning 3632 clear bottom assay plates containing 40 µl assay binding buffer or cold GLP-1 (NSB at 1 µM final). Then, 90 µl membranes (1 µg/well), 50 µl $^{125}$I-GLP-1 (0.15 nM final concentration in reaction), and 50 µl of WGA beads (150 µg/well) are added. Plates are sealed, mixed end over end, and read with a MicroBeta scintillation counter after 12 hr of settling time at room temperature.

Results are calculated as a percent of specific $^{125}$I-GLP-1 binding in the presence of compound. The Absolute $IC_{50}$ concentration of compound is derived by non-linear regression of percent specific binding of $^{125}$I-GLP-1 vs. the concentration of compound added. The $IC_{50}$ concentration is converted to Ki using the Cheng-Prusoff equation (Cheng Y., Prusoff W. H., Biochem. Pharmacol. 22, 3099-3108, 1973). The Ki of the OXM peptide analogue of SEQ ID NO: 3 wherein the Cys(PEG20k) at position 39 is amidated was 1540±158 nM for hGLP-1R binding.

EXAMPLE 5

Glucagon Receptor-Stimulated cAMP Functional Assay

The Glucagon stimulated cAMP functional assay uses the same cloned hGcgR expressing cell line as used for the hGcgR binding assay described above in Example 3. Cells are stimulated with the OXM peptide analogue, and the cAMP generated within the cell is quantitated using an Amplified Luminescent Proximity Homogeneous Assay (Alpha Screen) from Perkin Elmer (6760625R). Briefly, cAMP induced within the cell competes for binding of biotinylated cAMP from the kit to a coated anti-cAMP antibody Acceptor bead and a strepavidin coated Donor bead. As the cAMP level within the cell increases, a disruption of the Acceptor bead-biotinylated cAMP-Donor bead complex occurs and decreases the signal which is observed.

The hGcgR-HEK293 cells are harvested from sub-confluent tissue culture dishes with Enzyme-Free Cell Dissociation Solution, (Specialty Media 5-004-B). The cells are pelleted at low speed and washed 3 times with assay buffer [25 mM HEPES in Hank's buffered salt solution (HBSS)-with Mg and Ca (GIBCO, 14025-092) with 0.1% Fatty Acid Free BSA] then diluted to a final concentration of 125,000 cells per ml. Biotinylated cAMP from the Alpha Screen kit is added to the diluted cells at a final concentration of 1 unit/0.04 ml. A phosphodiesterase inhibitor, IBMX (250 mM in dimethyl sulfoxide (DMSO)), is also added to the diluted cells to a final concentration of 500 uM. Glucagon is initially dissolved in 0.01 N HCl at 1 mg/ml and immediately frozen at –80° C. Upon thawing, the glucagon should be used within 1 hr. The glucagon, cAMP standard, and OXM peptide analogue are serially diluted into Assay buffer to a 6× final concentration. The functional assay is performed in 96 well, low-volume, white, polystyrene Costar Plates (3688). The reaction starts by adding 0.01 ml of the diluted OXM peptide analogue, glucagon, or cAMP into 0.04 ml of the cell mixture. After one hour at room temperature, the reaction is stopped by the addition of 0.03 ml of Lysis Buffer [10 mM HEPES, pH 7.4, 1% NP40, and 0.01% fatty acid free BSA containing 1 unit each/0.03 ml of Acceptor and Donor beads from the Alpha Screen Kit]. Addition of the lysis buffer is performed in the dark to prevent bleaching of the detection beads. The plates are wrapped in foil, gently shaken for 1 minute then left to equilibrate overnight at room temperature. The plates are read on a Perkin-Elmer Envision instrument. The Alpha screen units are converted into pmoles cAMP generated per well based upon the cAMP standard curve. The pmoles cAMP generated in each well is converted to a percent of the maximal response observed with the glucagon control. An $EC_{50}$ value is derived by non-linear regression analysis using the percent maximal response vs. the concentration of peptide added. The OXM peptide analogue of SEQ ID NO: 3 wherein the Cys(PEG20k) at position 39 is amidated, like wild type OXM, was fully efficacious and potent at hGcgR with $EC_{50}$ of 60.0±2.97 nM.

EXAMPLE 6

Glucagon-Like-Peptide 1 (hGLP-1) Receptor-Stimulated cAMP Functional Assay

The GLP-1 stimulated cAMP functional assay uses the same cloned hGLP-1R expressing cell line as used for the hGLP-1R binding assay described above in Example 4. Cells are stimulated with the OXM peptide analogue, and the cAMP generated within the cell is quantitated using an Amplified Luminescent Proximity Homogeneous Assay (Alpha Screen) from Perkin Elmer (6760625R). Briefly, cAMP induced within the cell competes for binding of biotinylated cAMP from the kit to a coated anti-cAMP antibody Acceptor bead and a strepavidin coated Donor bead. As the cAMP level within the cell increases, a disruption of the Acceptor bead-biotinylated cAMP-Donor bead complex occurs and decreases the signal which is observed.

The hGLP-1R-HEK293 cells are harvested from sub-confluent tissue culture dishes with Enzyme-Free Cell Dissociation Solution, (Specialty Media 5-004-B). The cells are pelleted at low speed and washed 3 times with assay buffer [25 mM HEPES in HBSS-with Mg and Ca (GIBCO, 14025-092) with 0.1% Fatty Acid Free BSA] then diluted to a final concentration of 125,000 cells per ml. Biotinylated cAMP from the Alpha Screen kit is added to the diluted cells at a final concentration of 1 unit/0.04 ml. A phosphodiesterase inhibitor, IBMX (250 mM in DMSO), is also added to the diluted cells to a final concentration of 500 µM. GLP-1 is stored at 1 mg/ml in PBS as frozen aliquots at –80° C. The GLP-1, cAMP standard, and OXM peptide analogue are serially diluted into Assay buffer to a 6× final concentration. The functional assay is performed in 96 well, low volume, white, polystyrene Costar Plates (3688). The reaction starts by adding 0.01 ml of the diluted OXM peptide analogue, GLP-1, or cAMP into 0.04 ml of the cell mixture. After 1 hr at room temperature, the reaction is stopped by the addition of 0.03 ml of Lysis Buffer [10 mM HEPES, pH 7.4, 1% NP40, and 0.01% fatty acid free BSA containing 1 unit each/0.03 ml of Acceptor and Donor beads from the Alpha Screen Kit]. Addition of the lysis buffer is performed in the dark to prevent bleaching of the detection beads. The plates are wrapped in foil, gently shaken for 1 minute then left to equilibrate overnight at room temperature. The plates are read on a Perkin-Elmer Envision instrument. The Alpha screen units are converted into pmoles cAMP generated per well based upon the cAMP standard curve. The pmoles cAMP generated in each well is converted to a percent of the maximal response observed with the GLP-1 control. An $EC_{50}$ value is derived by non-linear regression analysis using the percent maximal response vs. the concentration of peptide added. The OXM peptide analogue of SEQ ID NO: 3 wherein the Cys(PEG20k) at position 39 is amidated, like wild type OXM, was fully efficacious and potent at hGLP-1R with $EC_{50}$ of 6.58±0.87 nM.

EXAMPLE 7

Effects on Food Intake, Body Weight and Body Composition in Diet-induced Obese (DIO) Mice Three to four months old male diet-induced obese (DIO) mice are individually housed in a temperature-controlled (24°

C.) facility with a 12 hour light/dark cycle (lights on 22:00), and have free access to food and water. After 2 weeks acclimation to the facility, mice are randomized to treatment groups (n=8-10/group), each group having similar mean body weight and fat mass. Mice are subcutaneously (sc) injected with vehicle solution and weighed for 2 days to acclimate them to the procedures.

Cumulative weight loss of the 7.5 nmole/kg group was similar to that observed with the positive control, which is about 6% reduction when compared to the vehicle group. Vehicle controlled cumulative weight loss of the 15 and 30 nmole/kg groups were 10% and 15% respectively. Body composition analysis showed that the weight loss was primarily due to loss of fat mass (Table 1).

TABLE 1

Weight change in DIO mice over a 14-day treatment period
(mean ± SEM; n = 8)

| Dose of OXM peptide analogue of SEQ ID NO: 3 wherein the Cys(PEG20k) at position 39 is amidated (nmole/kg) | Overall weight loss (g weight change for 14 days) | Total food intake (g total for 14 days) | Fat mass loss (g fat weight change for 14 days) |
|---|---|---|---|
| 0 (Vehicle) | 0.7 ± 0.2 | 39.6 ± 0.7 | 0.4 ± 0.2 |
| 7.5 | −1.7 ± 0.3* | 36.5 ± 1.2* | −1.1 ± 0.3* |
| 15 | −3.5 ± 0.3* | 31.4 ± 0.9* | −2.7 ± 0.2* |
| 30 | −5.6 ± 0.4* | 29.0 ± 1.3* | −4.0 ± 0.3* |

Vehicle or OXM peptide analogue (dose range 7.5-30 nmole/kg) dissolved in vehicle is administered by sc injection to ad libitum fed DIO mice 30-90 minutes prior to the onset of the dark cycle every 3 days for 2 weeks (two repeated studies). Body weight and the weight of food plus the hopper are measured at the same time. Food consumed in the preceeding 24 hours is calculated by subtracting current weight of food plus the hopper from that of the previous day. Absolute changes in body weight are calculated by subtracting the body weight of the animal prior to the first injection. On days 1 and 14 total fat mass is measured by nuclear magnetic resonance (NMR) using an Echo Medical System (Houston, Tex.) instrument. Fat free mass is calculated by subtracting fat mass from total body weight.

Study 1

The OXM peptide analogue of SEQ ID NO: 3 wherein the Cys(PEG20k) at position 39 is amidated is administered by subcutaneous injection to 4 months old male diet-induced obese (DIO) mice. The OXM peptide analogue is injected once every 3 days for 2 weeks at doses of 7.5, 15 and 30 nmole/kg and compared to vehicle treated mice and positive control (7.5 nmole/kg of a long-acting GLP-1R agonist injected every 3 days) treated animals.

Treatment with the OXM peptide analogue of SEQ ID NO: 3 wherein the Cys(PEG20k) at position 39 is amidated produced a dose-dependent reduction in food intake and body weight. At the end of 2-week study period, cumulative food intake in the 15 and 30 nmole/kg groups was reduced by 21% and 27%, respectively when compared to the vehicle group.

Study 2

The OXM peptide analogue of SEQ ID NO: 3 wherein the Cys(PEG20k) at position 39 is amidated (7.5 or 22.5 nmole/kg) and positive control (7.5 or 22.5 nmole/kg of a long-acting GLP-1R agonist) are administered every 3 days by subcutaneous injection to 4 months old male diet-induced obese (DIO) C57BL/6 for 2 weeks.

All treated groups exhibited significantly decreased cumulative food intake relative to vehicle controls. The OXM peptide analogue and positive control decreased body weight to similar degrees, about 5% and 10% for the low and high doses, respectively. Body composition analysis confirmed that weight loss associated with the OXM peptide analogue and positive control is primarily due to loss of fat mass (Table 2).

TABLE 2

Weight change in DIO over a 14-day treatment period
(mean ± SEM; n = 10)

| Dose of OXM peptide analogue of SEQ ID NO: 3 wherein the Cys(PEG20k) at position 39 is amidated (nmole/kg) | Overall weight loss (g weight change for 14 days) | Total food intake (g total for 14 days) | Fat mass loss (g fat weight change for 14 days) |
|---|---|---|---|
| 0 (Vehicle) | 0.1 ± 0.2 | 38.8 ± 0.5 | 0.0 ± 0.2 |
| 7.5 | −2.5 ± 0.3* | 33.3 ± 0.6* | −1.6 ± 0.2* |
| 22.5 | −5.2 ± 0.2* | 28.7 ± 0.6* | −3.8 ± 0.2* |

These data show that the OXM peptide analogue of SEQ ID NO: 3 wherein the Cys(PEG20k) at position 39 is amidated decreased cumulative food intake and body weight in two repeated 14 day DIO mouse studies, compared to vehicle-treated mice. Reduced body weight was primarily due to reduction in fat mass.
*p < 0.05 versus vehicle (Dunnett's test)

EXAMPLE 8

Effects on Blood Glucose Excursion During an Intraperitoneal Glucose Tolerance Test or an Oral Glucose Tolerance Test after 2-week Treatment in DIO Mice Fifty-six hours after the fifth injection as described in Example 7 in DIO mice, mice are fasted for 16 hours prior to the start of the glucose tolerance test. At time 0, animals are given 2 g/kg dextrose by oral gavage (Table 3, Study 1) or intraperitoneal (IP) injection (Table 4, Study 2). Blood is collected by tail vein bleeding at 0, 15, 30, 60 and 120 minutes after glucose challenge. Glucose concentration is measured by glucometer. All doses of the OXM peptide analogue of SEQ ID NO: 3 wherein the Cys(PEG20k) at position 39 is amidated as well as the positive control significantly lowered the blood glucose at all time points measured before and after the oral glucose challenge when compared to the vehicle-treated controls.

TABLE 3

Effects of OXM peptide analogue of SEQ ID NO: 3 wherein the Cys(PEG20k) at position 39 is amidated on the blood glucose excursion following administration of an oral glucose load

| Dose of OXM peptide analogue of SEQ ID NO: 3 wherein the Cys(PEG20k) at position 39 is amidated (nmole/kg) | Glucose AUC (mg*min/dL) | |
|---|---|---|
| | MEAN | SEM |
| 0 (Vehicle) | 24786 | 1127 |
| 7.5 | 13802* | 264 |
| 15 | 12668* | 209 |
| 30 | 13056* | 293 |

Data given as area under the glucose curve
(= integrated values from t + 0 to 120 min) (n = 7)
These data show that the OXM peptide analogue of SEQ ID NO: 3 wherein the Cys(PEG20k) at position 39 is amidated significantly reduced the blood glucose excursion following an oral glucose load. Statistical significance evaluated by Dunnett's test.
(*p < 0.05 vs. vehicle)

TABLE 4

Effects of OXM peptide analogue of SEQ ID NO: 3 wherein the Cys(PEG20k) at position 39 is amidated on the blood glucose excursion following an intraperitoneal (ip) glucose load

| Dose of OXM peptide analogue of SEQ ID NO: 3 wherein the Cys(PEG20k) at position 39 is amidated (nmole/kg) | Glucose AUC (mg*min/dL) | |
|---|---|---|
| | MEAN | SEM |
| 0 (Vehicle) | 32148 | 894 |
| 7.5 | 19198* | 2521 |
| 22.5 | 15720* | 1054 |

Data given as area under the glucose curve
(= integrated values from t + 0 to 120 min) (n = 6)
These data show that the OXM peptide analogue of SEQ ID NO: 3 wherein the Cys(PEG20k) at position 39 is amidated significantly reduced the blood glucose excursion following an intraperitoneal (ip) glucose load. Statistical significance evaluated by Dunnett's test.
(*p < 0.05 vs. vehicle)

EXAMPLE 9

Effects on Blood Glucose Excursion During an Intraperitoneal Glucose Tolerance Test in Lean Mice Nine week old male C57BL/6 mice are used in the study Animals are randomized into groups based on fed body weight. Animals are injected with vehicle or OXM peptide analogue (dose 5.0-15.0 nmole/kg) 16 hours prior to the start of the test. Food is removed at the time of injection of peptide or vehicle. At time 0, animals are given 2 g/kg dextrose by IP injection. Blood is collected by tail vein bleeding at 0, 3, 6, 12 and 30 minutes after glucose challenge. Glucose concentration is measured by glucometer. Insulin is measure by Mesoscale.

Both doses of the OXM peptide analogue of SEQ ID NO: 3 wherein the Cys(PEG20k) at position 39 is amidated significantly lowered blood glucose excursion (Table 5) and significantly increased plasma insulin concentrations (Table 6) when compared to the vehicle-treated controls.

TABLE 5

Effects of OXM peptide analogue of SEQ ID NO: 3 wherein the Cys(PEG20k) at position 39 is amidated on blood glucose excursion following an intraperitoneal (ip) glucose tolerance test in lean mice

| Dose of OXM peptide analogue of SEQ ID NO: 3 wherein the Cys(PEG20k) at position 39 is amidated (nmole/kg) | Glucose AUC (mg*min/dL) | |
|---|---|---|
| | MEAN | SEM |
| Vehicle | 9816 | 532 |
| 5 | 6287* | 720 |
| 15 | 6881* | 331 |

Data given as area under the glucose curve
(= integrated values from t + 0 to 30 min) (n = 6)
These data show that the OXM peptide analogue of SEQ ID NO: 3 wherein the Cys(PEG20k) at position 39 is amidated significantly reduced the blood glucose excursion following an intraperitoneal (ip) glucose tolerance test in lean mice. Statistical significance evaluated by Dunnett's test.
(*p < 0.05 vs. vehicle)

TABLE 6

Effects of OXM peptide analogue of SEQ ID NO: 3 wherein the Cys(PEG20k) at position 39 is amidated on plasma insulin concentration following an intraperitoneal (ip) glucose tolerance test in lean mice

| Dose of OXM peptide analogue of SEQ ID NO: 3 wherein the Cys(PEG20k) at position 39 is amidated (nmole/kg) | Insulin AUC (ng*min/mL) | |
|---|---|---|
| | MEAN | SEM |
| 0 (Vehicle) | 9.44 | 0.80 |
| 5 | 33.29* | 5.88 |
| 15 | 58.32* | 8.86 |

Data given as area under the insulin curve
(= integrated plasma insulin values from t + 0 to 30 min) (n = 6)
These data show that the OXM peptide analogue of SEQ ID NO: 3 wherein the Cys(PEG20k) at position 39 is amidated significantly increased plasma insulin AUC following an intraperitoneal (ip) glucose tolerance test in lean mice. Statistical significance evaluated by Dunnett's test.
(*p < 0.05 vs. vehicle)

EXAMPLE 10

Effects on Blood Glucose Excursion During an Oral Glucose Tolerance Test (OGTT) or an Intraperitoneal (IP) Glucose Tolerance Test (IPGTT) in Obese (ob/ob) Mice Two to three months old male ob/ob mice are individually housed in a temperature-controlled (24° C.) facility with a 12 hour light/dark cycle (lights on 2200 hours), and have free access to food and water. After at least 2 weeks of acclimation to the facility, 3-hours fasting blood glucose is measured by tail vein bleeding at 9 AM. Mice with blood glucose under 180 mg/dL are not used. Remaining animals are randomized to treatment groups (N=7/group), each group having similar average blood glucose level. The mice are given access to food until the time of injection. Animals are injected with vehicle, 7.5 nmole/kg or 15 nmole/kg OXM peptide analogue at 4 PM of the same day. Food is removed at the time of injection. An OGTT (Table 7) or IPGTT (Table 8) is performed 16 hours after the peptide injection. At time 0, animals are given 2 g/kg dextrose by oral gavage (Table 7) or intraperitoneal injection (Table 8). Blood is collected by tail vein bleeding at 0, 15, 30, 60 and 120 minutes after glucose challenge. Blood glucose concentration is measured by glucometer. A single injection of the OXM peptide analogue of SEQ ID NO: 3 wherein the Cys(PEG20k) at position 39 is amidated normalized blood glucose in ob/ob mice. Glucose levels at all time points measured after glucose challenge were significantly lower than that in the vehicle control group.

TABLE 7

Effects of OXM peptide analogue of SEQ ID NO: 3 wherein the Cys(PEG20k) at position 39 is amidated on blood glucose excursion following an oral glucose tolerance test in ob/ob mice

| Dose of OXM peptide analogue of SEQ ID NO: 3 wherein the Cys(PEG20k) at position 39 is amidated (nmole/kg) | Glucose AUC (mg*min/dL) | |
|---|---|---|
| | MEAN | SEM |
| 0 (Vehicle) | 32885 | 5341 |
| 7.5 | 12103* | 1864 |
| 15 | 14837* | 2322 |

Data given as area under the glucose curve
(= integrated values from t + 0 to 120 min) (n = 7)
These data show that the OXM peptide analogue of SEQ ID NO: 3 wherein the Cys(PEG20k) at position 39 is amidated significantly reduced the blood glucose excursion following an oral glucose tolerance test in ob/ob mice. Statistical significance evaluated by Dunnett's test.
(*p < 0.05 vs. vehicle)

TABLE 8

Effects of OXM peptide analogue of SEQ ID NO: 3 wherein the Cys(PEG20k) at position 39 is amidated on blood glucose excursion following an intraperitoneal (ip) glucose tolerance test in ob/ob mice

| Dose of OXM peptide analogue of SEQ ID NO: 3 wherein the Cys(PEG20k) at position 39 is amidated (nmole/kg) | Glucose AUC (mg*min/dL) | |
|---|---|---|
| | MEAN | SEM |
| 0 (Vehicle) | 37894 | 1482 |
| 7.5 | 16944* | 1821 |

Data given as area under the glucose curve
(= integrated values from t + 0 to 120 min) (n = 7)
These data show that the OXM peptide analogue of SEQ ID NO: 3 wherein the Cys(PEG20k) at position 39 is amidated significantly reduced the blood glucose excursion following an intraperitoneal (ip) glucose tolerance test in ob/ob mice. Statistical significance evaluated by Dunnett's test.
(*p < 0.05 vs. vehicle)

EXAMPLE 11

Acute Effects on Plasma Glucose, Triglyceride Levels, and Hepatic Gene Expression in Male Diet-induced Obese C57BL/6 Mice In order to investigate metabolic pathways that are modulated by treatment with the OXM peptide analogue of SEQ ID NO: 3 wherein the Cys(PEG20k) at position 39 is amidated independent of weight loss related changes, the OXM peptide analogue and a positive control (a long acting GLP-1R agonist) are administered by subcutaneous injection to 3 month old male diet-induced obese (DIO) mice. The day before the study, mice are randomized to treatment groups (N=7/group), each group having similar mean body weight. That same night (approximately 10 PM), animals are placed into clean cages and dosed with vehicle, 22.5 nmole/kg of the OXM peptide analogue, or 22.5 nmole/kg of the positive control by subcutaneous injection. Food is removed at the time of injection of peptide or vehicle. The following morning (approximately 10 AM), the animals are sacrificed to collect plasma and liver tissue. Plasma glucose and triglyceride concentrations are measured using a Hitachi blood chemistry analyzer. Gene expression is determined by RT-PCR. Malonyl-CoA levels are measured by HPLC.

After a single injection, plasma glucose was significantly decreased relative to vehicle control in all treatment groups. Plasma triglyceride level was decreased relative to vehicle control only in mice treated with the OXM peptide analogue of SEQ ID NO: 3 wherein the Cys(PEG20k) at position 39 is amidated but not in those treated with the long-acting GLP-1R agonist. In addition, hepatic pgc-1α gene expression was significantly increased by 45%, and liver malonyl-CoA concentrations were significantly decreased by 30% in mice treated with the OXM peptide analogue of SEQ ID NO: 3 wherein the Cys(PEG20k) at position 39 is amidated relative to vehicle controls. The OXM peptide analogue of SEQ ID NO: 3 wherein the Cys(PEG20k) at position 39 is amidated significantly decreased hepatic PCSK9 gene expression relative to vehicle controls.

We claim:

1. An Oxyntomodulin peptide analogue comprising the amino acid sequence:

(SEQ ID NO: 5)
His-(D-Ser)-Gln-Gly-Thr-Phe-Thr-Ser-Asp-(1-Nal)-

Ser-Lys-Tyr-Leu-Asp-Glu-Lys-Ala-Ala-Gln-Glu-Phe-

Val-Gln-Trp-Leu-Leu-Asn-(Aib)-Ala-Arg-Asn-Arg-

Asn-Asn-Ile-Ala-Xaa$_{38}$-Xaa$_{39}$ wherein Xaa$_{38}$ is Cys, Cys-PEG, or is absent; Xaa$_{39}$ is Cys, Cys-PEG, or is absent;

and wherein the C-terminal amino acid is optionally amidated.

2. The Oxyntomodulin peptide analogue according to claim 1, comprising the amino acid sequence:

(SEQ ID NO: 2)
His-(D-Ser)-Gln-Gly-Thr-Phe-Thr-Ser-Asp-(1-Nal)-

Ser-Lys-Tyr-Leu-Asp-Glu-Lys-Ala-Ala-Gln-Glu-Phe-

Val-Gln-Trp-Leu-Leu-Asn-(Aib)-Ala-Arg-Asn-Arg-

Asn-Asn-Ile-Ala-Cys-Cys wherein the Cys residue at position 38 is optionally PEGylated; and wherein the Cys residue at position 39 is optionally PEGylated.

3. The Oxyntomodulin peptide analogue according to claim 2, wherein the analogue is PEGylated on the thiol of the Cys residue at either position 38 or position 39 with an approximately 40 kDa PEG molecule.

4. The Oxyntomodulin peptide analogue according to claim 2, wherein the analogue is PEGylated on the thiol of both Cys residues at positions 38 and 39 with an approximately 20 kDa PEG molecule in each case and comprises the amino acid sequence:

(SEQ ID NO: 3)
His-(D-Ser)-Gln-Gly-Thr-Phe-Thr-Ser-Asp-(1-Nal)-

Ser-Lys-Tyr-Leu-Asp-Glu-Lys-Ala-Ala-Gln-Glu-Phe-

Val-Gln-Trp-Leu-Leu-Asn-(Aib)-Ala-Arg-Asn-Arg-

Asn-Asn-Ile-Ala-Cys(PEG20k)-Cys(PEG20k)

5. The Oxyntomodulin peptide analogue according to claim 4, wherein each PEG molecule is linear.

6. The Oxyntomodulin peptide analogue according to claim 5, wherein each PEG molecule is attached to the Cys residue by an maleimide linker moiety.

7. The Oxyntomodulin peptide analogue according to claim 6, wherein the carboxyl group of the Cys residue at position 39 is amidated.

8. A method of treating obesity in a subject in need thereof, comprising administering to the subject an effective amount of an Oxyntomodulin peptide analogue according to claim 7.

9. The Oxyntomodulin peptide analogue according to claim 1, wherein the Cys residue at position 39 is absent, and the Cys residue at position 38 is PEGylated with an approximately 40 kDa PEG molecule.

10. A pharmaceutical composition comprising the Oxyntomodulin peptide analogue of claim 1, and a pharmaceutically acceptable carrier, diluent, or excipient.

11. A method of treating non-insulin-dependent diabetes in a subject in need thereof, comprising administering to the subject an effective amount of an Oxyntomodulin peptide analogue according to claim 1.

12. A method of treating obesity in a subject in need thereof, comprising administering to the subject an effective amount of an Oxyntomodulin peptide analogue according to claim 1.

13. A pharmaceutical composition comprising the Oxyntomodulin peptide analogue of claim 7, and a pharmaceutically acceptable carrier, diluent, or excipient.

14. A method of treating non-insulin-dependent diabetes in a subject in need thereof, comprising administering to the subject an effective amount of an Oxyntomodulin peptide analogue according to claim 7.

15. An Oxyntomodulin peptide analogue according to Formula 3

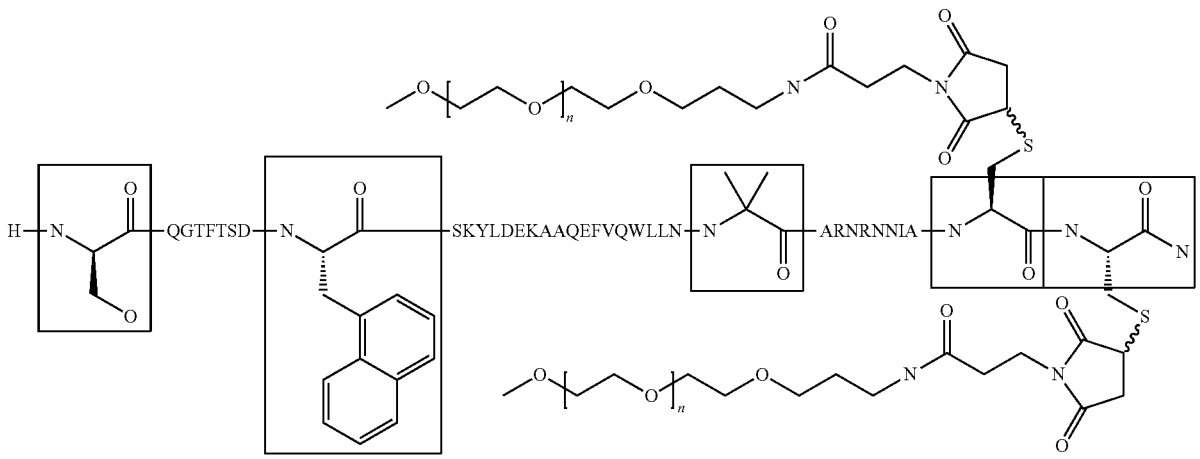

n = 425-475

16. A pharmaceutical composition comprising the Oxyntomodulin peptide analogue of claim 15, and a pharmaceutically acceptable carrier, diluent, or excipient.

17. A method of treating non-insulin-dependent diabetes in a subject in need thereof, comprising administering to the subject an effective amount of an Oxyntomodulin peptide analogue according to claim 15.

18. A method of treating obesity in a subject in need thereof, comprising administering to the subject an effective amount of an Oxyntomodulin peptide analogue according to claim 15.

* * * * *

SEQUENCE LISTING

```
<160> NUMBER OF SEQ ID NOS: 5

<210> SEQ ID NO 1
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is D-Ser
<220> FEATURE:
<221> NAME/KEY: MISC_FEATURE
<222> LOCATION: (10)..(10)
<223> OTHER INFORMATION: Xaa at position 10 is 1-Nal
<220> FEATURE:
<221> NAME/KEY: MISC_FEATURE
<222> LOCATION: (29)..(29)
<223> OTHER INFORMATION: Xaa at position 29 is Aib
<400> SEQUENCE: 1
His Xaa Gln Gly Thr Phe Thr Ser Asp Xaa Ser Lys Tyr Leu Asp Glu
1               5                   10                  15
```

Lys Ala Ala Gln Glu Phe Val Gln Trp Leu Leu Asn Xaa Ala Arg Asn
            20                  25                  30

Arg Asn Asn Ile Ala
            35

<210> SEQ ID NO 2
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is D-Ser
<220> FEATURE:
<221> NAME/KEY: MISC_FEATURE
<222> LOCATION: (10)..(10)
<223> OTHER INFORMATION: Xaa at position 10 is 1-Nal
<220> FEATURE:
<221> NAME/KEY: MISC_FEATURE
<222> LOCATION: (29)..(29)
<223> OTHER INFORMATION: Xaa at position 29 is Aib

<400> SEQUENCE: 2

His Xaa Gln Gly Thr Phe Thr Ser Asp Xaa Ser Lys Tyr Leu Asp Glu
1               5                   10                  15

Lys Ala Ala Gln Glu Phe Val Gln Trp Leu Leu Asn Xaa Ala Arg Asn
            20                  25                  30

Arg Asn Asn Ile Ala Cys Cys
            35

<210> SEQ ID NO 3
<211> LENGTH: 39
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is D-Ser
<220> FEATURE:
<221> NAME/KEY: MISC_FEATURE
<222> LOCATION: (10)..(10)
<223> OTHER INFORMATION: Xaa at position 10 is 1-Nal
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MISC_FEATURE
<222> LOCATION: (38)..(38)
<223> OTHER INFORMATION: Xaa at position 38 is Cys
<220> FEATURE:
<221> NAME/KEY: MOD_RES
<222> LOCATION: (38)..(38)
<223> OTHER INFORMATION: Xaa at position 38 is modified by 20kDa PEG
<220> FEATURE:
<221> NAME/KEY: MISC_FEATURE
<222> LOCATION: (39)..(39)
<223> OTHER INFORMATION: Xaa at position 39 is Cys
<220> FEATURE:
<221> NAME/KEY: MOD_RES
<222> LOCATION: (39)..(39)
<223> OTHER INFORMATION: Xaa at position 39 is modified by 20kDa PEG
<220> FEATURE:
<221> NAME/KEY: MOD_RES
<222> LOCATION: (39)..(39)
<223> OTHER INFORMATION: Xaa at position 39 may be amidated
<400> SEQUENCE: 3
His Xaa Gln Gly Thr Phe Thr Ser Asp Xaa Ser Lys Tyr Leu Asp Glu
1               5                   10                  15

```
Lys Ala Ala Gln Glu Phe Val Gln Trp Leu Leu Asn Xaa Ala Arg Asn
            20                  25                  30

Arg Asn Asn Ile Ala Xaa Xaa
        35
```

<210> SEQ ID NO 4
<211> LENGTH: 37
<212> TYPE: PRT
<213> ORGANISM: Artificial sequence
<220> FEATURE:
<223> OTHER INFORMATION: Synthetic Construct

<400> SEQUENCE: 4

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```

<210> SEQ ID NO 5
<211> LENGTH: 39
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is D-Ser
<220> FEATURE:
<221> NAME/KEY: MISC_FEATURE
<222> LOCATION: (10)..(10)
<223> OTHER INFORMATION: Xaa at position 10 is 1-Nal
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MISC_FEATURE
<222> LOCATION: (38)..(38)
<223> OTHER INFORMATION: Xaa at position 38 is Cys or is absent
<220> FEATURE:
<221> NAME/KEY: MOD_RES
<222> LOCATION: (38)..(38)
<223> OTHER INFORMATION: Xaa at position 38 may be modified by 20kDa PEG
      or 40kDa PEG
<220> FEATURE:
<221> NAME/KEY: MISC_FEATURE
<222> LOCATION: (39)..(39)
<223> OTHER INFORMATION: Xaa at position 39 is Cys or is absent
<220> FEATURE:
<221> NAME/KEY: MOD_RES
<222> LOCATION: (39)..(39)
<223> OTHER INFORMATION: Xaa at position 39 may be modified by 20kDa PEG
      or 40kDa PEG
<220> FEATURE:
<221> NAME/KEY: MOD_RES
<222> LOCATION: (39)..(39)
<223> OTHER INFORMATION: Xaa at position 39 may be amidated

<400> SEQUENCE: 5

```
His Xaa Gln Gly Thr Phe Thr Ser Asp Xaa Ser Lys Tyr Leu Asp Glu
1               5                   10                  15

Lys Ala Ala Gln Glu Phe Val Gln Trp Leu Leu Asn Xaa Ala Arg Asn
            20                  25                  30

Arg Asn Asn Ile Ala Xaa Xaa
        35
```